US006889090B2

(12) United States Patent
Kreindel

(10) Patent No.: US 6,889,090 B2
(45) Date of Patent: May 3, 2005

(54) SYSTEM AND METHOD FOR SKIN TREATMENT USING ELECTRICAL CURRENT

(75) Inventor: Michael Kreindel, Haifa (IL)

(73) Assignee: Syneron Medical Ltd., Or Akiva (IL)

( * ) Notice: Subject to any disclaimer, the term of this patent is extended or adjusted under 35 U.S.C. 154(b) by 157 days.

(21) Appl. No.: 09/988,816

(22) Filed: Nov. 20, 2001

(65) Prior Publication Data

US 2003/0097162 A1 May 22, 2003

(51) Int. Cl.7 .................................................. A61F 2/00
(52) U.S. Cl. ..................................... 607/101; 607/102
(58) Field of Search ...................... 607/96–102; 606/41, 606/42, 32–33; 604/21

(56) References Cited

U.S. PATENT DOCUMENTS

| | | | |
|---|---|---|---|
| 5,318,563 A | * 6/1994 | Malis et al. ................... 606/38 |
| 5,584,863 A | * 12/1996 | Rauch et al. ................... 607/2 |
| 5,755,753 A | 5/1998 | Knowlton | |
| 5,846,252 A | 12/1998 | Mehl, Sr. | |
| 5,865,787 A | * 2/1999 | Shapland et al. ............. 604/21 |
| 6,156,031 A | * 12/2000 | Aita et al. ..................... 606/33 |
| 6,228,081 B1 | * 5/2001 | Goble ........................... 606/34 |
| 6,350,276 B1 | * 2/2002 | Knowlton ................... 607/104 |
| 6,383,184 B1 | * 5/2002 | Sharkey ........................ 606/41 |
| 6,413,255 B1 | * 7/2002 | Stern ............................ 606/41 |
| 6,416,514 B1 | * 7/2002 | Ein-Gal ........................ 606/49 |

* cited by examiner

*Primary Examiner*—Roy D. Gibson
(74) *Attorney, Agent, or Firm*—Browdy and Neimark, P.L.L.C.

(57) ABSTRACT

A system and method for selective thermal treatment of skin irregularities. The system comprises one or more RF electrodes that are adapted to apply RF energy to the skin. An RF pulse generator generates voltage pulses in the RF range at the electrodes, where the voltage pulses have a duration of 2–500 ms. The method comprises applying RF electrodes to the skin and generating voltage pulses at the electrodes in the RF range, where the pulses have a duration in the range of 2–500 ms.

20 Claims, 3 Drawing Sheets

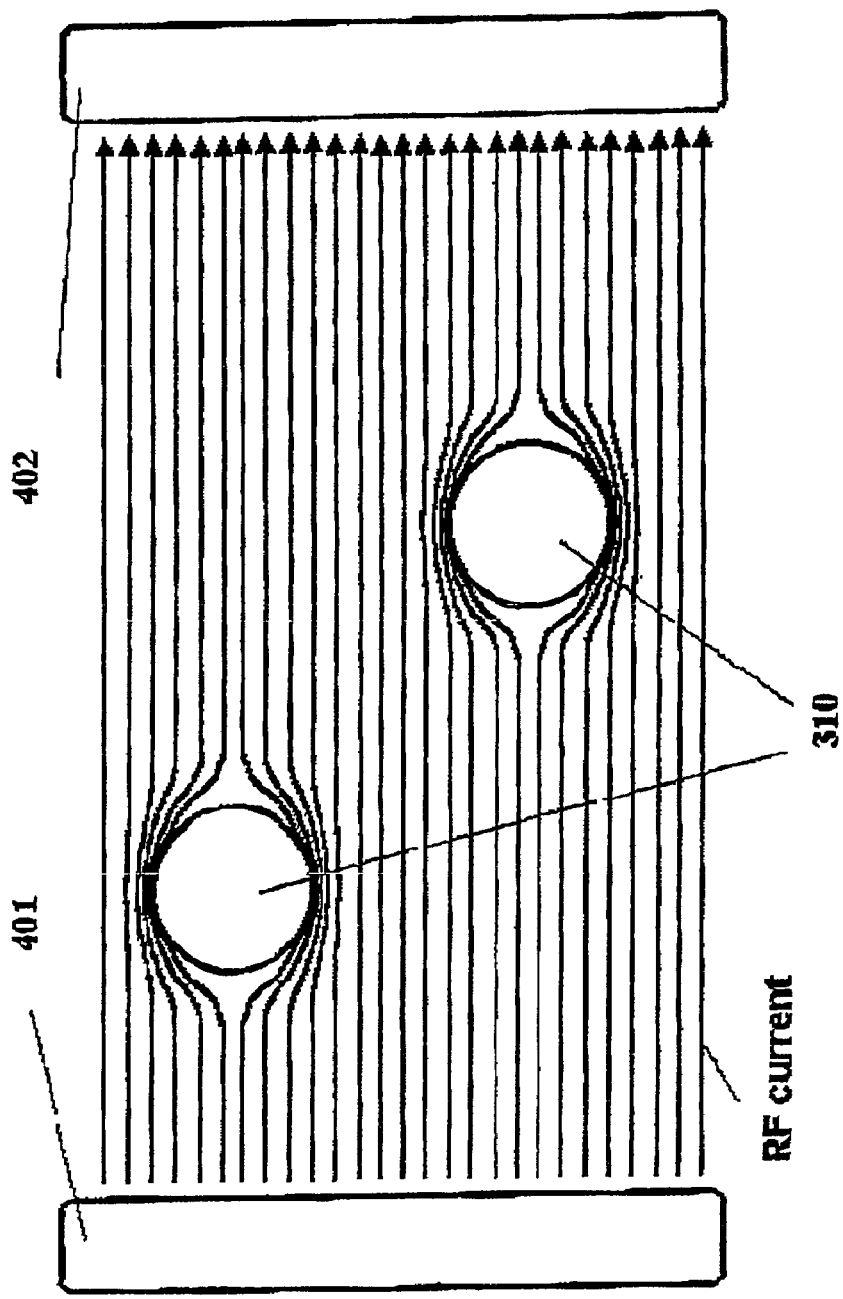

SYSTEM AND METHOD FOR SKIN TREATMENT USING ELECTRICAL CURRENT

FIELD OF THE INVENTION

This invention relates to methods and systems for treating skin.

BACKGROUND OF THE INVENTION

Selective thermal treatment of skin irregularities such as treatment of vascular lesions, removal of unwanted hair or improving skin texture is commonly used in aesthetic medicine. In order to be destroyed, the target the must be raised to a temperature of about 70° C. without raising the temperature of the epidermis or dermis to damaging levels. The most popular method of thermal skin treatment is selective photo-thermolysis in which light energy produced by a laser or flash lamp is used. However, in many cases it is not possible to heat the skin irregularity to a temperature necessary for destroying it without heating the surrounding skin to damaging levels. The main problem is that he optical contrast between the skin irregularity and the surrounding skin tissue is often not high enough to obtain a significant difference in temperature between the skin irregularity and the surrounding skin tissue. In these cases, another form of energy should be found to provide selective heating of skin irregularity without damaging the surrounding tissue.

U.S. Pat. No. 5,755,753 discloses use of the radio-frequency (RF) range of electro-magnetic energy for skin tightening, where RF energy is applied to a pre-cooled skin surface. U.S. Pat. No. 5,846,252 discloses treating hairs to reduce their electrical resistance and then applying RF current.

SUMMARY OF THE INVENTION

The present invention is based upon the unexpected finding that pulsed applications of RF energy selectively heats skin irregularities to a temperature that destroys it without raising the surrounding skin temperature to damaging levels.

The present invention thus provides a method and apparatus for dermatological treatment of skin irregularities in which pulsed RF energy is applied, to the skin to beat a skin irregularity. The invention may be used for cosmetic treatment of any complicated skin irregularity such as hair removal, skin rejuvenation, vascular or pigmented lesions, and treatment of collagen abnormalities. The system includes an applicator with one or more electrodes for applying RF currents to the skin. A RF pulse generator is used to apply pulsed RF current to the skin by the electrodes, either directly or through a conductive substance. The frequency of the RF is preferably at least 300 kHz in order to prevent tissue spasms. A RF current pulse may consist of a train of shorter pulses.

Heat generation during the application of the RF is higher near the skin surface. In order to make heating uniform within the skin, the surface is preferably cooled during treatment. The surface may be cooled by applying a cooled substance such as ice or ethanol to the skin or by using a thermoelectric cooler. The skin is preferably hydrated in order to enhance the penetration of the cooling into the deep layers of the skin, as is known in the art. When the skin is externally cooled at the surface, the RF energy can heat the target to a depth of up to a few millimeters.

The RF electrodes may optionally be used to monitor skin impedance during the treatment. Since increasing skin temperature leads to a change in impedance, monitoring the skin impedance allows the temperature distribution in the skin to be followed so that the parameters of the treatment may be determined so as to optimize the treatment. Such parameters may include, for example, the pulse duration of the RF energy, the frequency of the RF energy, the power of the RF energy, the delay time between cooling the skin and the application of the RF energy. The temperature distribution in the skin depends on the delay between the cooling, the application of the RF energies, and the selection of pulse parameters. The temperature distribution within the skin may thus be controlled by controlling the delay between the time the cooling is applied, and the time the RF is applied. A microprocessor may be used for determining the optimal delay time (t) in response to a selected skin temperature profile. This may be calculated as is known in the art, for example, using the equation $t=d^2/(4A)$, where d is the cooling depth, which in this case is about equal to the thickness of the epidermis (0.1 mm), and A is the skin diffusivity (about $1.4\times10^{-3}$ cm$^2$/sec) Alternatively or additionally, the temperature distribution may be controlled by controlling the pulse duration of the RF energy as is known in the art, for example, as disclosed in Ross et al., theoretical considerations in laser hair removal. IN Dermatologic Clinics, W.B. Saunders Company, Volume 17, pages 333–335, 1999.

The invention provides a system for selective thermal treatment of skin irregularities comprising:

(i) one or more RF electrodes adapted to apply RF energy to the skin; and (ii) An RF pulse generator configured to generate pulses of current in the RF range, the voltage pulses having a duration of 2–500 ms.

The invention further provides a system wherein the one or more parameters are selected from the group comprising a pulse duration of the RF energy, a frequency of the RF energy, a power of the RF energy, a delay time between cooling the skin and application of the RF energy.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 3 shows current distribution around hair shafts.

DETAILED DESCRIPTION OF AN EMBODIMENT OF THE INVENTION

Figure 1:
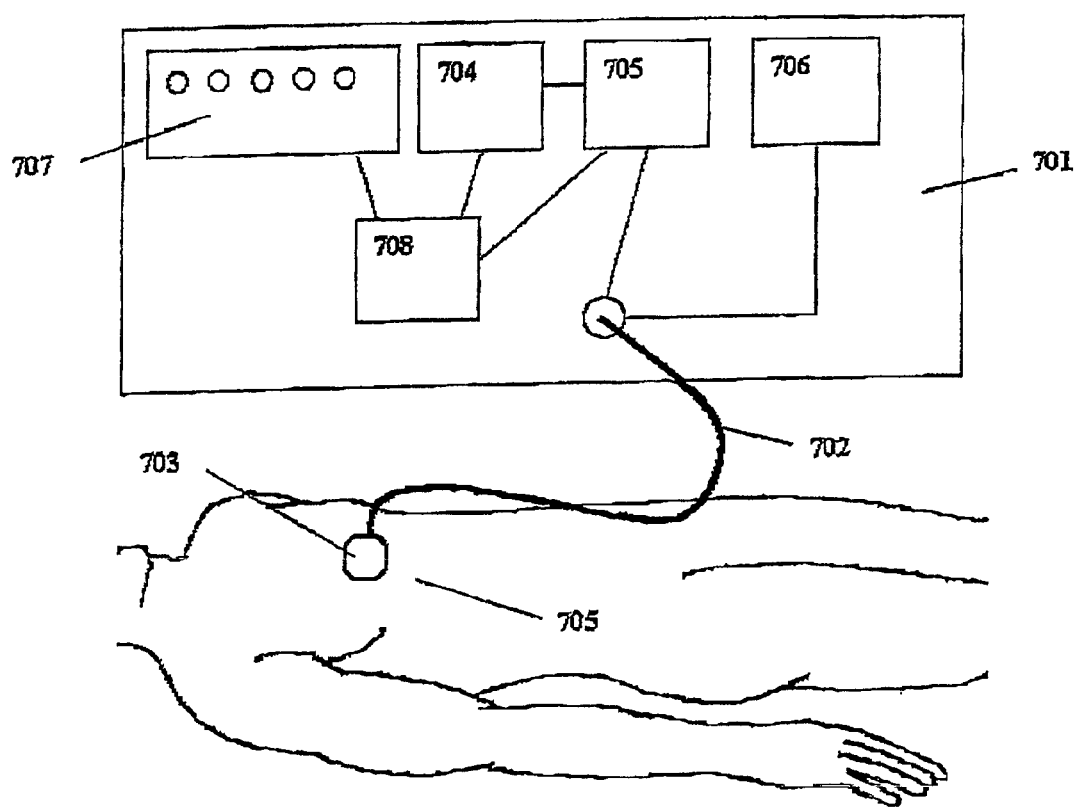
FIG. 1 shows a system for applying pulsed RF energy to an individual in accordance with the invention.

Referring first to FIG. 1, a system is shown for applying pulsed RF energy in accordance with one embodiment of the invention. An applicator 703, to be described in detail below, contains a pair of RF electrodes and cooling system. The applicator 703 is adapted to be applied to the skin of an individual 710 in the region to be treated. The applicator 703 is connected to a control unit 701 via a cable 702. The control unit 701 includes a power source 708. The power source 708 is connected to an RF generator 705 that is connected to the RF electrodes in the applicator 703 via wires in the cable 702. The control unit 701 contains a cooling system 712 that cools a fluid such as ethanol or water for cooling the applicator 703. The cooled fluid flows from the cooling system 712 to the applicator via a first tube in the cable 702, and flows from the applicator 703 back to the refrigeration unit via a second tube in the cable 702. The control unit 701 has an input system such as a keypad 707 that allows an operator to input selected values of parameters of the treatment, such as the frequency, pulse duration and intensity of the RF energy or the wavelength and intensity of the optical energy. The control unit 701 optionally contains a processor 704 for monitoring and controlling various functions of the system. For example, the processor 704 may monitor the electrical impedance between the electrodes in the applicator 703, and determine the temperature distribution in the skin in the vicinity of the applicator 703. The processor 704 may also determine the parameters of the treatment based upon the impedance measurements.

Figure 2:
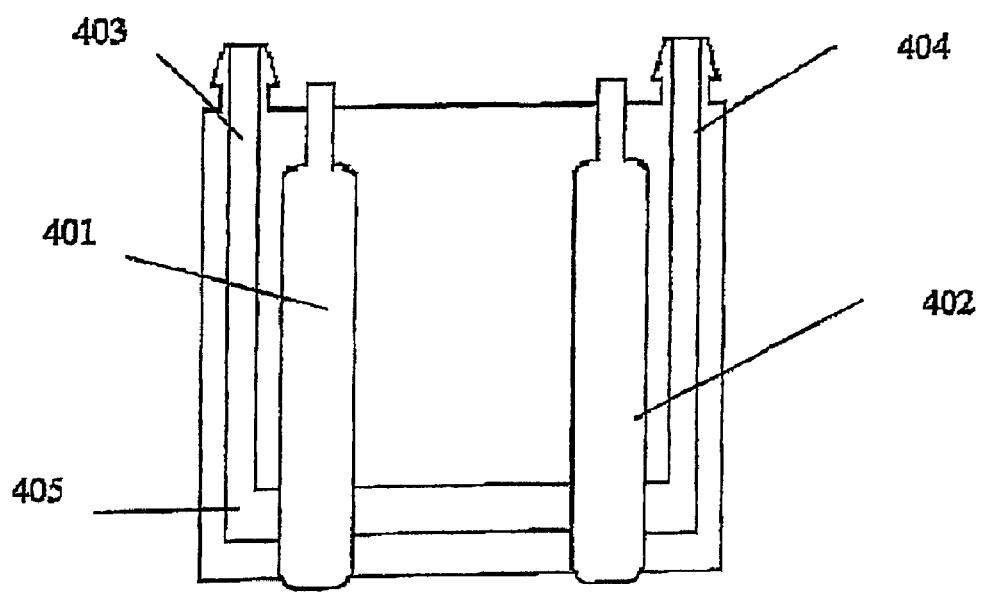
FIG. 2 shows an applicator with two electrodes and a cooling system.

FIG. 2 shows the applicator 703 in detail. The applicator contains a pair of electrodes 401 and 402 that apply RF energy to the skin. The housing and electrodes are cooled by fluid cooled by the cooling system 706 that flows in a tube 405 between inlet 403 and outlet 404. The inlet 403 and the outlet 404 are connected to the cooling system 706 via the first and second tubes in the cable 702.

Using the system shown in FIG. 3 to apply RF energy to a treated site having a size typically of at least 2 mm$^2$, the following exemplary parameter values may be used:

Frequency of the RF energy: from about 300 kHz to about 100 MHz.

Output power of the RF energy: from about 5 to about 500 W.

Duration of the irradiation: from about 1 to about 500 msec.

Pulse repetition rate: from about 0.1 to about 10 pulses per second.

FIG. 3 shows the RF current distribution between the two electrodes 401 and 402 that is obtained using the system of FIGS. 1 and 2 with the above exemplary parameter values. Hair shafts such as the a shaft 31 se in cross section in FIG. 3, have a higher resistively then the surrounding skin so the electrical current curves around the shafts concentrating in a 3 micrometer layer around each shaft. Detailed calculation using Maxwell equations and empirical coefficients (S. Gabriel, et al., The dielectric properties of biological tissues: III. Parametric models for dielectric spectrum of tissues. *Phys. Med. Biol.* 41:2271–2293, 1996) shows that the current density in a hair follicle is twice the current density in the surrounding tissue. The heat generation H is proportional to square of the current density j, $H=\sigma j^2$, where $\sigma$ is conductivity of skin. Thus, heating of a hair is about four times higher than the skin heating.

What is claimed is:

1. A system for selective thermal treatment of skin irregularities on a surface of the skin comprising:
   (i) two or more RF electrodes adapted to apply RF energy to the surface of the skin;
   (ii) a RF pulse generator configured to generate pulses of current in the RF range, the pulses having a duration of 2–500 ms; and
   (iii) a cooling unit adapted to cool the skin;
   wherein the pulse of the RF current consists of a train of shorter pulses.

2. The system according to claim 1 wherein the cooling unit comprises a thermoelectric cooler.

3. The system according to claim 1 further comprising a impedance meter for measuring an impedance across one or more of the RE electrodes.

4. The system according to claim 3 further comprising a processor configured to determine a heat distribution in the skin based upon one or more impedance measurements.

5. The system according to claim 4 wherein the processor is further configured to determine one or more parameters of the RF energy based upon one or more impedance measurements.

6. The system according to claim 5 wherein the one or more parameters are selected from the group comprising a pulse duration of the RF energy, a frequency of the RE energy, a power of the RE energy, and a delay time between cooling the skin an application of the RE energy.

7. The system according to claim 1 further comprising input means for determining one or more parameters of the RF energy.

8. The system according to claim 7 wherein the one or more parameters are selected from the group comprising a pulse duration of the RF energy, a frequency of the RF energy, a power of the RF energy, a delay time between cooling the skin and application of the RF energy.

9. A method for selective thermal treatment of skin irregularities comprising:
   (i) applying one or more RF electrodes to the skin;
   (ii) generating current pulses in the RF range, the pulses having a duration in the range of 2–500 ms; and
   (iii) cooling the skin;
   wherein the pulse of the RF current consists of a train of shorter pulses.

10. The method according to claim 9 wherein cooling the skin involves cooling a fluid and allowing the fluid to flow near the skin.

11. The method according to claim 9 wherein cooling the skin is performed with a thermoelectric cooler.

12. The method according to claim 9 further comprising measuring an impedance across one or more RF electrode pairs.

13. The method according to claim 12 further comprising determining a heat distribution in the skin based upon one or more impedance measurements.

14. The method according to claim 13 further comprising determining one or more parameters of the RF energy based upon one or more impedance measurements.

15. The method according to claim 14 wherein the one or more parameters are selected from the group comprising a pulse duration of the RF energy, a frequency of the RF energy, a power of the RF energy, a delay time between cooling the skin an application of the RF energy.

16. The method according to claim 9 wherein a frequency of the RF energy is from about 300 kHz to about 100 MHz.

17. The method according to claim 9 wherein an output power of the RF energy is from about 5 to about 500 W.

18. The method according to claim 9 wherein a pulse repetition rate is from about 0.1 to about 10 pulses per second.

19. The method according to claim 9 further comprising hydrating the skin.

20. The method according to claim 9 wherein the skin irregularity is selected from the group comprising a hair, a vascular or pigmented lesion and a collagen abnormality.

* * * * *